US012648980B2

(12) United States Patent
Shin et al.

(10) Patent No.: US 12,648,980 B2
(45) Date of Patent: Jun. 9, 2026

(54) COMPOSITION FOR PREVENTING OR AMELIORATING BROMHIDROSIS COMPRISING SEED FERMENTATION PRODUCT OF PLANT BELONGING TO THE GENUS Lotus

(71) Applicant: COSMAX INC., Gyeonggi-Do (KR)

(72) Inventors: Jae Ho Shin, Daegu (KR); Min Ji Kim, Daegu (KR); Min Chul Kim, Daegu (KR); Jai Hyun So, Daegu (KR); Hyung Woo Jo, Seongnam (KR); Kyu Young Shim, Seoul (KR); Dong Geol Lee, Hwaseong (KR); Seung Hyun Kang, Seoul (KR)

(73) Assignee: COSMAX INC., Gyeonggi-Do (KR)

( * ) Notice: Subject to any disclaimer, the term of this patent is extended or adjusted under 35 U.S.C. 154(b) by 517 days.

(21) Appl. No.: 18/108,754

(22) PCT Filed: Jun. 29, 2021

(86) PCT No.: PCT/KR2021/008182
§ 371 (c)(1),
(2) Date: Feb. 13, 2023

(87) PCT Pub. No.: WO2022/039379
PCT Pub. Date: Feb. 24, 2022

(65) Prior Publication Data
US 2024/0016872 A1     Jan. 18, 2024

(30) Foreign Application Priority Data

Aug. 18, 2020    (KR) ........................ 10-2020-0103243

(51) Int. Cl.
*A61K 36/48*      (2006.01)
*A61P 17/00*      (2006.01)
*C12R 1/23*       (2006.01)

(52) U.S. Cl.
CPC .............. *A61K 36/48* (2013.01); *A61P 17/00* (2018.01); *A61K 2236/19* (2013.01); *C12R 2001/23* (2021.05)

(58) Field of Classification Search
CPC ..... A61K 36/48; A61K 2236/19; A61P 17/00; C12R 2001/23
See application file for complete search history.

(56) References Cited

U.S. PATENT DOCUMENTS

2006/0251596 A1    11/2006    Akiba et al.
2008/0193570 A1     8/2008    Lee
2011/0311661 A1    12/2011    Behr et al.

FOREIGN PATENT DOCUMENTS

CN     106691895 A  *  5/2017    ............. A61K 8/347
JP     2005298489 A    10/2005
JP     2008520588 A     6/2008
KR     100797974 B1     1/2008

OTHER PUBLICATIONS

Liu et al. Increasing Antiradical Activity of Polyphenols from Lotus Seed Epicarp by Probiotic Bacteria Bioconversion. Molecules 2018, 23(10), . pp. 1-12. https://doi.org/10.3390/molecules23102667 (Year: 2018).*
Wang et al. Long-Term Safety and Efficacy of Botulinum Toxin A Treatment in Adolescent Patients with Axillary Bromhidrosis. Aesth Plast Surg 2018, 42:560-564 (Year: 2018).*
Wikipedia "*Lotus* (genus)" (wayback machine: dated Feb. 24, 2020); p. 1-7.*
The Gardener's Apprentice "Bird's-Foot Trefoil" Jul. 13, 2009; p. 1-3.*
Notice of Non-Final Rejection, dated Sep. 13, 2022, issued in corresponding Korean Application No. 20-103243, 4 pps.
Kim, Min Ji, et al, "Effect of bioconverted product of *Lotus corniculatus* seed on the axillary microbiome and body odor", Scientific Reports, Nature, 2021, pp. 1-14.
Saito et al., "Soy Isoflavone Genistein Inhibits an Axillary Osmidrosis Risk Factor ABCC11: In Vitro Screening and Fractional Approach for ABCC11-Inhibitory Activities in Plant Extracts and Dietary Flavonoids", Nutrients, pp. 1-19, D2. Nutrients.
Steele et al., "Flavonoids in seed and root exudates of *Lotus pedunculatus* and their biotransformation", Physiologia Plantarum, 1999, pp. 1-8, D1. Physiologia Plantarum.
Schreurs et al., "Skatole and indole concentration and the odour of fat from lambs . . . ", ScienceDirect, Animal Feed Science and Technology, Elsevier, D5. Animal Feed Science and Technology, 2007, pp. 254-271.
Supplementary European Search Report, issued on Jul. 25, 2024, in corresponding European Application No. 21858467, 4 pages.

* cited by examiner

*Primary Examiner* — Bethany P Barham
(74) *Attorney, Agent, or Firm* — Panitch Schwarze Belisario & Nadel LLP

(57)    ABSTRACT

Provided is a composition for preventing or ameliorating bromhidrosis, including a seed fermentation product of a plant belonging to the genus *Lotus*. The composition may inhibit production of substances related to bromhidrosis by reducing proportions of microorganisms of the genus *Corynebacterium* and the genus *Anaerococcus*, which are related to bromhidrosis, in the microbiome.

6 Claims, 5 Drawing Sheets

COMPONENTS OF SEED FERMENTATION PRODUCT OF
*LOTUS CORNICULATUS*

RESULTS OF MEASURING ODOR INTENSITIES

GROUP TREATED WITH SEED
FERMENTATION PRODUCT OF
*LOTUS CORNICULATUS*

UNTREATED GROUP

CHANGES IN AXILLARY MICROBIAL COMMUNITY IN GROUP TREATED WITH SEED FERMENTATION PRODUCT OF LOTUS CORNICULATUS AND UNTREATED GROUP

COMPOSITION FOR PREVENTING OR AMELIORATING BROMHIDROSIS COMPRISING SEED FERMENTATION PRODUCT OF PLANT BELONGING TO THE GENUS *Lotus*

TECHNICAL FIELD

The present disclosure relates to a composition for preventing or ameliorating bromhidrosis including a seed fermentation product of a plant belonging to the genus *Lotus*.

BACKGROUND ART

Body odor is a unique odor generated in the process of decomposition of sweat and waste products secreted by sweat glands distributed in the human body by microorganisms, etc., and may vary depending on race, gender, age, and the like.

Among various sources of body odor, secretions from apocrine sweat glands, which are mainly distributed in areas with a lot of body hair, such as the axillae, are high in fat, protein, sebum, and body waste, and in the process of decomposition of these secretions by microorganisms, an unpleasant smell called axillary odor may be generated. Bromhidrosis may be aggravated by secretion of sweat and sebum caused by strenuous exercise or stress, or certain types of food consumed, and furthermore, foods with strong odors, drinks containing a lot of caffeine, drinking alcohol, and smoking may also aggravate bromhidrosis.

General methods of suppressing bromhidrosis include a masking method and a method of using antiperspirants. Among them, the masking method is a method of concealing bromhidrosis by using a different scent. However, when a wrong scent is used to cover up the bromhidrosis, a stronger odor may be caused. In addition, the use of antiperspirants suppresses the bromhidrosis by using chemicals that act on the apocrine sweat glands, but it also shows side effects of increasing sweat and odor in other areas where there was no problem.

Accordingly, there is a need for a natural substance-based medicine that fundamentally improves axillary odor by changing the microbiome that causes axillary odor and has few side effects.

DESCRIPTION OF EMBODIMENTS

Technical Problem

Provided according to an embodiment are a composition for preventing or ameliorating bromhidrosis including a seed fermentation product of a plant belonging to the genus *Lotus* and an external skin preparation including the composition.

Provided according to an embodiment is a method of preparing a composition for preventing or ameliorating bromhidrosis, including fermenting seeds of a plant of the genus *Lotus* with lactic acid bacteria.

Provided according to an embodiment is a method of preventing or treating bromhidrosis including administering to a subject any one of the above composition, the external skin preparation, and a composition prepared by the above preparation method.

Provided according to an embodiment is a use of any one of the composition, the external skin preparation, and a composition prepared by the preparation method for preventing or treating bromhidrosis.

Provided according to an embodiment is a use of any one of the composition, the external skin preparation, and a composition prepared by the preparation method for preparing a pharmaceutical composition for preventing or treating bromhidrosis.

Solution to Problem

An aspect of the present disclosure provides a composition for preventing or ameliorating bromhidrosis including a seed fermentation product of a plant belonging to the genus *Lotus*

In an embodiment of the present disclosure, the seed fermentation product of a plant belonging to the genus *Lotus* may inhibit decomposition activity of microorganisms belonging to the genus *Corynebacterium* and the genus *Anaerococcus*.

In addition, the seed fermentation product of a plant belonging to the genus *Lotus* may be fermented with lactic acid bacteria.

In an embodiment of the present disclosure, the lactic acid bacteria may be *Lactobacillus acidophilus*.

And, the fermentation may be performed for 3 days to 7 days at 35° C. to 37° C.

Another aspect of the present disclosure provides an external skin preparation for preventing or ameliorating bromhidrosis including the above composition.

In addition, an aspect of the present disclosure provides a method of preparing a composition for preventing or ameliorating bromhidrosis, including fermenting seeds of a plant of the genus *Lotus* with lactic acid bacteria.

Moreover, another aspect of the present disclosure provides a method of preventing or treating bromhidrosis including administering to a subject any one of the above composition, the external skin preparation, and a composition prepared by the above preparation method.

Furthermore, another aspect of the present disclosure provides a use of any one of the composition, the external skin preparation, and a composition prepared by the preparation method, for preventing or treating bromhidrosis.

Furthermore, another aspect of the present disclosure provides a use of any one of the composition, or a composition prepared by the preparation method, for preparing a pharmaceutical composition for preventing or treating bromhidrosis.

Advantageous Effects of Disclosure

By using the composition including a seed fermentation product of a plant belonging to the genus *Lotus* according to an embodiment, bromhidrosis may be effectively prevented or ameliorated.

BEST MODE

Figure 1:
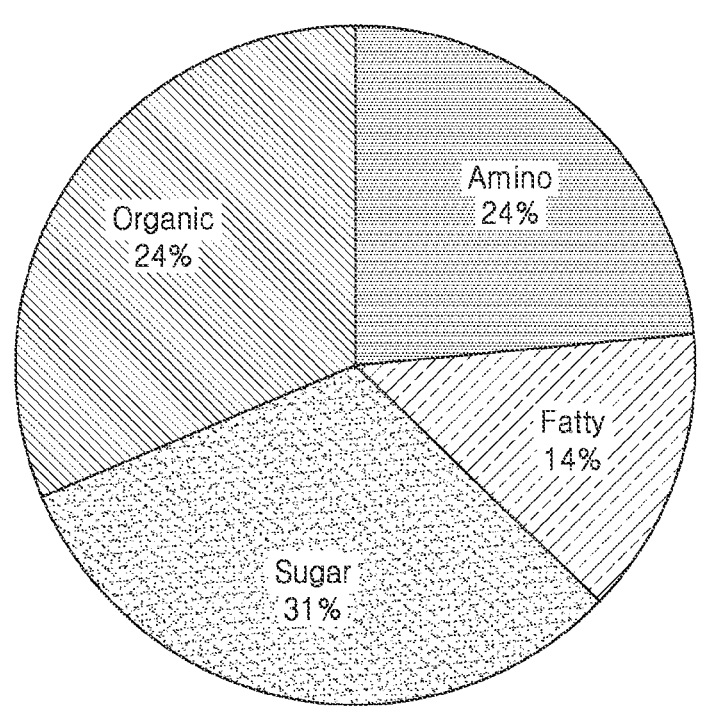
FIG. 1 shows results of analyzing components contained in a seed fermentation product of *Lotus corniculatus* by GC/TOF-MS.

An aspect provides a composition for preventing or ameliorating bromhidrosis including a seed fermentation product of a plant belonging to the genus *Lotus*.

The plant of the genus *Lotus* is a perennial plant belonging to the legume family. The plant belonging to the genus *Lotus* may include, for example, *Lotus corniculatus*, *Lotus pedunculatus*, and *Lotus uligninosus* native to Korea, but is not particularly limited thereto.

Plants of the genus *Lotus*, especially roots of *Lotus corniculatus*, are known to have antipyretic and hemostatic effects, and to have relieving effects on colds, sore throats, and colitis, however, an effect of ameliorating bromhidrosis of the seed fermentation product of *Lotus corniculatus* has not been known. The present inventors applied the seed fermentation product of *Lotus corniculatus* to axillae of patients with bromhidrosis, and confirmed that the seed fermentation product of *Lotus corniculatus* have an effect of ameliorating bromhidrosis by measuring odors before and after applying the seed fermentation product of *Lotus corniculatus*, surveying whether or not the bromhidrosis was improved, and confirming a change in distribution of microbiome.

The term "fermentation" refers to a process in which useful microorganisms proliferate in a composition containing components of seeds of a plant of the genus *Lotus*, and the components of the composition are changed by enzymes produced by the useful microorganisms.

According to an embodiment, the seed fermentation product of a plant belonging to the genus *Lotus* may reduce proportions of microorganisms that belong to the genera of *Corynebacterium* and *Anaerococcus* that produce substances that cause axillary odor in the skin microbiome. Alternatively, the seed fermentation product of a plant belonging to the genus *Lotus* may inhibit proliferation or activity of microorganisms belonging to the genus *Corynebacterium* and microorganisms belonging to the genus *Anaerococcus*. More specifically, the seed fermentation product of a plant belonging to the genus *Lotus* may lower the proportions of the genus *Corynebacterium* and the genus *Anaerococcus* in the microbiome present in the human axilla. According to FIG. 2, when the seed fermentation product of *Lotus corniculatus* was applied to the axilla of a patient with bromhidrosis, the proportions of microorganisms belonging to the genus *Corynebacterium* and microorganisms belonging to the genus *Anaerococcus* in the microbiome present in the axilla decreased. On the other hand, microorganisms belonging to the genus *Staphylococcus* rather increased. It is difficult to evaluate the reduction of microorganisms of the genus *Corynebacterium* and the genus *Anaerococcus* simply as a result of direct inhibition of the fermentation product of the microorganisms of the genus *Corynebacterium* and the genus *Anaerococcus*. This is because the change in the microbiome may be a result of an increase of growth or activity of other microorganisms or an effect on a third type of microorganisms interacting with the microorganisms of the genera *Corynebacterium* and *Anaerococcus*.

According to an embodiment, the seed fermentation product of a plant belonging to the genus *Lotus* may be fermented with lactic acid bacteria. The lactic acid bacteria may be, for example, *Lactobacillus rhamnosus*, *Lactobacillus bulgaricus*, *Lactobacillus casei*, *Lactobacillus plantarum*, *Lactobacillus acidophilus*, *Lactobacillus reuteri*, *Lactobacillus fermentum*, *Lactobacillus salivarius*, *Lactobacillus gasseri*, *Lactobacillus helveticus*, *Lactobacillus paracasei*, *Bifidobacterium bifidium*, *Bifidobacterium breve*, *Bifidobacterium longum*, *Bifidobacterium animalis*, *Lactococcus lactis*, *Enterococcus faecium*, *Enterococcus faecalis*, or *Streptococcus thermophilus*. The lactic acid bacteria are strains that are widely used in probiotics products and may be easily obtained or purchased by those skilled in the art.

The seed fermentation product of *Lotus corniculatus* may be a fermented product of the seed of a plant of the genus *Lotus* itself or an extract of the seed. Specifically, a target of the fermentation may be unprocessed seeds, dried seeds, powdered seeds, seed extracts, or seed concentrates, and is not particularly limited.

For example, the seed extract of a plant of the genus *Lotus* may be extracted by pulverizing the seed of the plant of the genus *Lotus*, and then immersing the same in water, C1 to C4 lower alcohols, or a mixed solvent thereof. The seed extract may be extracted at room temperature or in a heated condition, and the heated condition may be about at 40° C. to about 100° C. The room temperature may be about 15° C. to about 40° C., about 15° C. to about 30° C., about 15° C. to about 25° C., or about 20° C. The extraction may be performed for about 36 hours to about 168 hours, about 36 hours to about 60 hours, about 36 hours to about 50 hours, or about 36 hours to about 48 hours. As an extraction method, extraction methods known in the art such as solvent extraction, ultrasonic extraction, filtration, and reflux extraction may be used, but is not limited thereto. The extraction process may be repeated several times, and then additional processes such as concentration or lyophilization may be performed.

The seed fermentation product of a plant belonging to the genus *Lotus* may be prepared by inoculating lactic acid bacteria into a liquid medium including a seed extract of a plant of the genus *Lotus* as a main component and fermenting. Fermentation conditions may be appropriately determined depending on a type of the lactic acid bacteria, for example, fermentation may be performed by culturing the bacteria at 37° C. for 72 hours. The seed fermentation product of a plant belonging to the genus *Lotus* may be a supernatant or a precipitate obtained by centrifuging the culture medium after inoculating a strain.

According to an embodiment, the *Lactobacillus acidophilus* may be a strain deposited under an accession number of KCTC13233BP.

Fermentation conditions may be adjusted according to the type of lactic acid bacteria used and an amount and concentration of the seed extract of the plant of the genus *Lotus*. According to an embodiment, the fermentation may be performed at about 35° C. to about 37° C. for about 3 days to about 7 days when using *Lactobacillus acidophilus*.

The composition may be used by applying a predetermined amount to the axilla area and then wiping off. A time for leaving the composition after an application to the axilla is not particularly limited, and a user may properly adjust the time in consideration of simplicity of use and maximization of effect.

Another aspect provides an external skin preparation for preventing or ameliorating bromhidrosis including the above composition.

The external skin preparation may be prepared in any formulation commonly prepared in the art, and for example, formulated as solutions, suspensions, emulsions, pastes, gels, creams, lotions, powders, soaps, surfactant-containing cleansers, oils, powder foundations, emulsion foundations, wax foundations, and sprays, but is not limited thereto. More specifically, the external skin preparation may be formulated into a toner, a nourishing lotion (milk lotion), a nourishing cream, a massage cream, an essence, an eye cream, a cleansing cream, a cleansing foam, a cleansing water, a pack, a spray, or a powder.

When the formulation of the external skin preparation is a paste, cream, or gel, animal oil, vegetable oil, wax, paraffin, starch, tragacanth, a cellulose derivative, polyethylene glycol, silicon, bentonite, silica, talc, or zinc oxide may be used as a carrier component.

When the formulation is a powder or a spray, lactose, talc, silica, aluminum hydroxide, calcium silicate, or polyamide powder may be used as a carrier component. In particular, when the formulation is a spray, a propellant such as chlorofluorohydrocarbon, propane/butane or dimethyl ether may be further included.

When the formulation is a solution or an emulsion, a solvent, a solubilizing agent or an emulsifying agent is used as a carrier component, for example, water, ethanol, isopropanol, ethyl carbonate, ethyl acetate, benzyl alcohol, benzyl benzoate, propylene glycol, 1,3-butyl glycol oil, glycerol aliphatic esters, polyethylene glycol, or sorbitan esters may be used.

When the formulation is a suspension, a liquid diluent such as water, ethanol, or propylene glycol, a suspension such as ethoxylated isostearyl alcohol, polyoxyethylene sorbitol ester, and polyoxyethylene sorbitan ester, microcrystalline cellulose, aluminum metahydroxide, bentonite, agar, or tragacanth, and the like may be used as a carrier component.

When the formulation is a surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaines, aliphatic alcohols, fatty acid glycerides, fatty acid diethanolamides, vegetable oils, lanolin derivatives, or ethoxylated glycerol fatty acid esters may be used as a carrier component.

The external skin preparation may be a cosmetic composition.

Another aspect provides a method of preparing a composition for preventing or ameliorating bromhidrosis, including fermenting seeds of a plant belonging to the genus *Lotus*, or a seed extract of a plant belonging to the genus *Lotus* with lactic acid bacteria.

The seed extract of the plant of the genus *Lotus* may be extracted by pulverizing seeds of *Lotus corniculatus*, and immersing the same in water, C1 to C4 lower alcohols, or a mixed solvent thereof. The *Lotus corniculatus* seed extract may be extracted at room temperature or in a heated condition, and the heated condition may be at about 40° C. to about 100° C.

The fermenting may be by inoculating lactic acid bacteria into a liquid medium containing a seed extract of a plant of the genus *Lotus* as a main component and fermenting.

Sterilizing seeds of the plant belonging to the genus *Lotus* or extracts thereof may be further included prior to the fermenting. The sterilization may be performed at about 55° C. to about 70° C. for about 20 minutes to about 60 minutes.

After the fermenting, obtaining a supernatant obtained by centrifuging the culture medium in which the inoculated strain is cultured may be further included.

Description of the lactic acid bacteria is the same as described above. For example, the lactic acid bacteria may be a strain of the genus *Lactobacillus*, specifically *Lactobacillus acidophilus*. The *Lactobacillus acidophilus* may be a strain deposited under an accession number of KCTC13233BP.

The fermentation may be adjusted according to the type of the lactic acid bacteria used, and the amount and concentration of the seed extract of *Lotus corniculatus*, for example, in the case of using *Lactobacillus acidophilus*, fermentation may be performed at about 35° C. to about 38° C. for 3 days to 7 days.

An aspect of the present disclosure provides a method of preventing or treating bromhidrosis including administering to a subject any one of the above composition, the external skin preparation, and a composition prepared by the above preparation method.

An aspect of the present disclosure provides a use of any one of the composition, the external skin preparation, and a composition prepared by the preparation method, for preventing or treating bromhidrosis.

An aspect of the present disclosure provides a use of any one of the composition, the external skin preparation, and a composition prepared by the preparation method, for preparing a pharmaceutical composition for preventing or treating bromhidrosis.

MODE OF DISCLOSURE

Hereinafter, one or more embodiments will be described in more detail through examples. However, these examples are intended to illustrate at least one embodiment, and the scope of the present disclosure is not limited to these examples.

Example 1: Preparation of Fermentation Product of *Lotus corniculatus*

1-1. Cultivation of Strain *Lactobacillus acidophilus*

A *Lactobacillus acidophilus* strain (hereinafter referred to as KNU-02 strain) deposited at the Biological Resource Center of the Korea Research Institute of Bioscience and Biotechnology under an accession number of KCTC13233BP was distributed. The KNU-02 strain was cultured in a Lactobacilli MRS broth medium for 24 hours, and then centrifuged at 7,000 rpm for 30 minutes in a centrifuge to obtain cells from which the supernatant was removed. The obtained cells were washed twice by using phosphate-buffered saline (PBS) (NaCl 0.8%, KCl 0.02%, $Na_2HPO_4$ 0.14%, and $KH_2PO_4$ 0.03%) sterilized at 121° C. for 15 minutes. The washed cells were then used for fermenting seeds of *Lotus corniculatus*.

1-2. Preparation of Seed Fermentation Product of *Lotus corniculatus* by Using *Lactobacillus acidophilus* KNU-02

Seeds of *Lotus corniculatus* were pulverized and then immersed in 1 L of 70% ethanol aqueous solution, which is used as an extraction solvent, and extracted at room temperature for 48 hours. After filtering the extracted solution with a filter paper, the filtrate was concentrated under reduced pressure by using a rotary evaporator to obtain a concentrated seed extract of *Lotus corniculatus*.

A liquid medium containing the seed extract of *Lotus corniculatus* as a main component was prepared, and 1 L of the liquid medium sterilized at 121° C. for 15 minutes was prepared to have a concentration of 100 mg/mL of the seed extract of *Lotus corniculatus*. The *Lactobacillus acidophilus* KNU-02 strain obtained in Example 1-1 was inoculated into 1 L of the liquid medium including the seed extract of *Lotus corniculatus*. The inoculated liquid medium was fermented at 37° C. for 72 hours (100 rpm), and when the culturing was finished, centrifuged by using a centrifuge (7,000 rpm, 30 minutes), and only the supernatant from which cells are removed was taken and filtered through a 0.2 μm filter to perform a filtration sterilization. Ethyl acetate including 0.1% acetic acid was added thereto at a ratio of 1:1, followed by solvent extraction for 48 hours and concentration by using a vacuum concentrator to obtain a fermentation product.

Example 2: Recruitment of Bromhidrosis Patients

Through the Global Medical Research Center, a total of 17 subjects were recruited, including 9 people suffering from bromhidrosis and 8 normal people who did not suffer from bromhidrosis. All of the subjects were women in their 30s to 50s.

The nine subjects suffering from bromhidrosis applied seed fermentation product of *Lotus corniculatus* to the axilla twice a day for one week. A use of other cosmetics, perfumes, and antibacterial soaps was restricted during the application period. (Hereinafter, the group may be referred of NaCl, and 0.2% agar powder and stored in a freezer at −80° C. until DNA extraction.

Example 3: Gene Search of *Lactobacillus acidophilus* KNU-02

Whole-genome sequencing was performed by using a PacBio Sequel equipment to identify genes related to production of antibacterial substance of *Lactobacillus acidophilus* KNU-02. The sequencing data were de novo assembled through the HGAP 4.0 Pipeline, and a total of 6 contigs were obtained. The six contigs were gene-annotated by using rapid annotations using subsystems technology (RAST). Through the gene annotation by using RAST, metabolic activity of *Lactobacillus acidophilus* KNU-02 was confirmed. As for subsystem coverage, 71% were open reading frames (ORFs) with defined subsystem classification, and the remaining 29% were ORFs without subsystem classification. Subsystem category distribution is specified in Table 1 below. *Lactobacillus acidophilus* was confirmed to have genes related to metabolism of carbohydrate and protein accounting for 32%. It is judged that since *Lactobacillus acidophilus* KNU-02 has a high expression rate of genes related to metabolism of carbohydrate and protein, *Lactobacillus acidophilus* KNU-02 is suitable for producing a product that affects axillary microbiome by decomposing polymer-type carbohydrate and protein molecules contained in the seeds of *Lotus corniculatus*.

TABLE 1

| Subsystem | Number of genes | Subsystem | Number of genes |
|---|---|---|---|
| Cofactors, vitamins, prosthetic groups, pigments | 48 | Regulation and cell signaling | 23 |
| Cell wall and capsule | 30 | Secondary metabolism | 1 |
| Virulence, disease, and defense | 36 | DNA metabolism | 46 |
| Potassium metabolism | 5 | Fatty acids, lipids, and isoprenoids | 23 |
| Photosynthesis | 0 | Nitrogen metabolism | 1 |
| Miscellaneous | 10 | Dormancy and sporulation | 6 |
| Phages, prophages, transposable elements, plasmids | 0 | Respiration | 12 |
| Membrane transport | 43 | Stress response | 6 |
| Iron acquisition and metabolism | 4 | Metabolism of aromatic compounds | 0 |
| RNA metabolism | 31 | Amino acids and derivatives | 91 |
| Nucleosides and nucleotides | 80 | Sulfur metabolism | 4 |
| Protein metabolism | 131 | Phosphorus metabolism | 15 |
| Cell division and cell cycle | 4 | Carbohydrates | 122 |
| Motility and chemotaxis | 0 | | | to as a group treated with the seed fermentation product of *Lotus corniculatus*.) Eight normal subjects did not use the seed fermentation product of *Lotus corniculatus*, and a use of other cosmetics, perfumes, and antibacterial soaps was restricted for one week (hereinafter referred to as an untreated group).

Skin microorganisms were collected from the axillae of the subjects immediately before and one week after the experiment. Specifically, skin microorganisms were collected by rubbing for about 3 minutes an area of about 50 cm² of the subject's axilla with a sterilized cotton swab soaked in a preservative solution. The cotton swabs that were used in collection of skin microorganisms were placed in a preservation solution including 0.1% Tween20, 0.15 M

Example 4: Analysis of Active Ingredients of Fermentation Product of *Lotus Corniculatus*

In order to confirm active ingredients of the fermentation product prepared in Example 1-2, analysis was conducted through GC/TOF-MS. The analysis of the active ingredients of each extract was repeated three times. And the mixture used in the analysis was also analyzed three times in the same way as the analysis of active ingredients for quality control of the analysis.

According to FIG. 1, it was confirmed that the components of the seed fermentation product of *Lotus corniculatus* were amino acids 24%, fatty acids 14%, carbohydrates (sugars) 31%, and other ingredients (organic) 24%, by mass.

Example 5: Measurement of Axillary Odor

Odor intensities of the group treated with the seed fermentation product of *Lotus corniculatus* and the untreated group were measured before and one week after participation in the experiment. Odor intensity was measured at a distance of 3 cm from the subject's axillary using an odor meter OMX-ADM equipped with a gas sensor. OMX-ADM is a device capable of measuring intensity of gases such as ethanol, acetone, hydrogen, and ammonia. The measured odor intensity is a value calculated according to the standards of the Ministry of the Environment of Japan.

Figure 2:
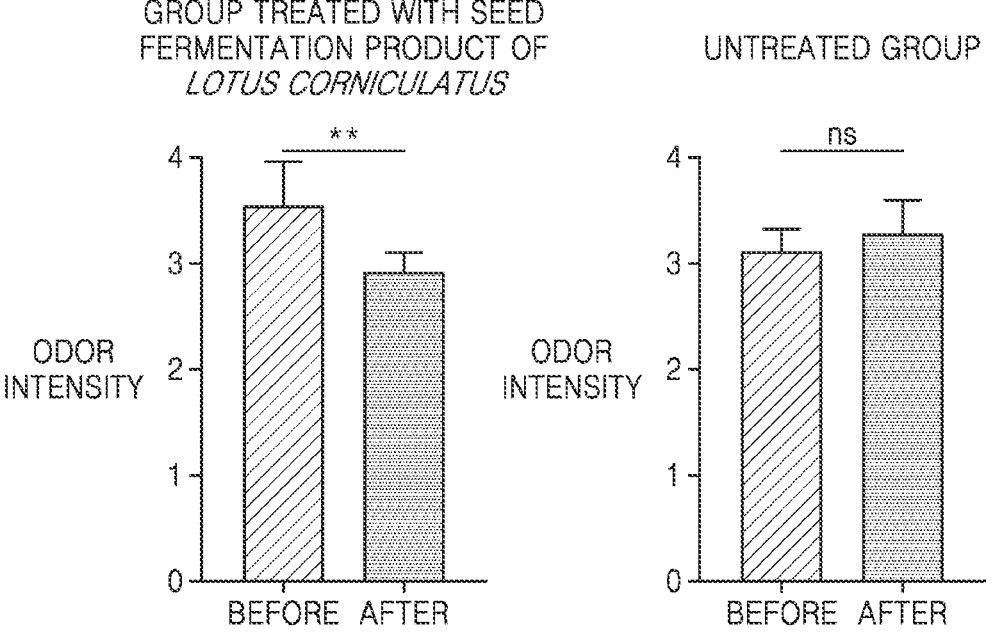
FIG. 2 shows results of measuring axillary odor intensities of subjects who used the seed fermentation product of *Lotus corniculatus* prepared according to an embodiment with an odor meter equipped with a gas measurement sensor.

FIG. 2 shows results of measuring odor intensities of the experimental group (treated group) before and one week after starting to use seed fermentation product of *Lotus corniculatus* and the untreated group before and one week after the participation in the experiment. According to FIG. 2, the average axillary odor intensity of the group treated with the seed fermentation product of *Lotus corniculatus* was decreased from 3.9 to 2.9. On the other hand, the odor intensity of the untreated group increased from 3.1 to 3.2. Therefore, it was confirmed that when a bromhidrosis patient uses the seed fermentation product of *Lotus corniculatus*, intensity of odor may be reduced to a level similar to that of a normal person.

Example 6: Evaluation of Senses of Improvement of Subjects

The group treated with the seed fermentation product of *Lotus corniculatus* and the untreated group were surveyed on the change of odor before and after participating in the experiment. Both groups were commonly surveyed on personal information, compliance with the application method, and concerns about axillary odor. In addition, the group treated with the seed fermentation product of *Lotus corniculatus* was surveyed on the axillary odor before and after application and whether or not there was an improvement, and the untreated group was surveyed on the degree of the axillary odor before and after participation in the experiment. A degree of axillary odor was classified into 5 levels: 'very strong (5 points)', 'strong (4 points)', 'normal (3 points)', 'weak (2 points)', and 'very weak (1 point)', and whether there was an improvement was evaluated in 2 levels as positive and negative. The degree of axillary odor and whether there was an improvement were based on subjective evaluation of the subject. The survey results are shown in Tables 2 and 3 below.

TABLE 2

| Group treated with seed fermentation product of Lotus corniculatus | Concerns about axillary odor | Degree of axillary odor before application (points) | Degree of axillary odor after application (points) | Improvement |
|---|---|---|---|---|
| S01 | Yes | 3 | 3 | Yes |
| S02 | Yes | 3 | 3 | Yes |
| S03 | Yes | 3 | 2 | Yes |
| S04 | Yes | 3 | 1 | Yes |
| S05 | Yes | 4 | 2 | Yes |
| S06 | Yes | 3 | 3 | Yes |
| S07 | Yes | 3 | 3 | Yes |
| S08 | Yes | 4 | 1 | Yes |
| S09 | Yes | 3 | 2 | Yes |

TABLE 3

| Untreated subjects | Concerns about axillary odor | Degree of axillary odor before participating in experiment | Degree of axillary odor after one week | — |
|---|---|---|---|---|
| S11 | No | 2 | 3 | — |
| S12 | No | 3 | 3 | — |
| S13 | No | 3 | 2 | — |
| S14 | No | 1 | 1 | — |
| S16 | No | 2 | 2 | — |
| S17 | No | 3 | 3 | — |
| S19 | No | 2 | 2 | — |
| S20 | No | 3 | 3 | — |

All nine participants in the group treated with the seed fermentation product of *Lotus corniculatus* complied with the application method and answered that there was no special side effect. According to Table 2, before the application of the fermentation product of *Lotus corniculatus*, two subjects answered 'strong (4 points)' for the degree of bromhidrosis, and six subjects answered 'normal (3 points)'. Nine out of nice people in the group treated with the seed fermentation product of *Lotus corniculatus* answered that axillary odor was improved by using the fermentation product.

According to Table 3, among the eight subjects in the untreated group, four subjects answered 'normal (3 points)' for the level of axillary odor before participating in the experiment, three subjects answered 'weak (2 points)', and one subject answered 'very weak'. (1 point)'. In the untreated group, there was no significant change in the ratio of responses for the degree of axillary odor after one week.

Figure 3:
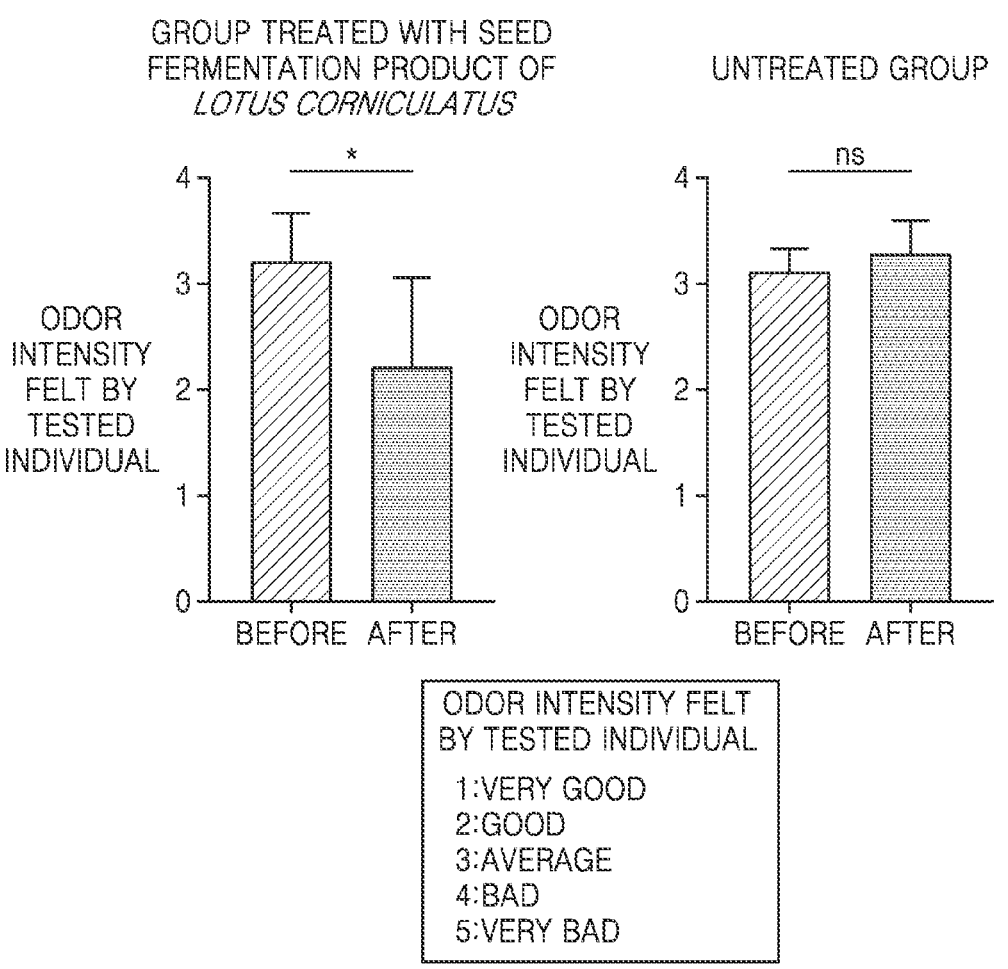
FIG. 3 shows results of a sensory test showing the sense of improvement of subjects who used the seed fermentation product of *Lotus corniculatus* prepared according to an embodiment.

FIG. 3 shows results of answers to whether or not the subjects felt improved in the survey conducted according to the above criteria. All nine subjects responded positively that their bromhidrosis was improved. According to FIG. 3, it was found that the untreated group almost did not feel any change in body odor during the experiment (ns), but it was confirmed that the degree of sensing that the body odor was improved after the experiment was significantly higher in the group treated with the seed fermentation product of *Lotus corniculatus*.

Example 7: Confirmation of Changes in Microbiome of Subjects with Improved Bromhidrosis Changes in the microbiome prepared in Example 1 were analyzed. Total DNA of microorganisms was extracted by using a PowerSoil DNA Pro Kit (QIAGEN, Germany), and the 16S rRNA V4-V5 region (515F: 5'-GTGCCAGCMGCCGCGG-3', 907R: 5'-CCGTCAAT-TCMTTTRAGTTT-3') was amplified by PCR. The amplified product was sequenced by using an Illumina MiSeq equipment. Operational taxonomic units (OTUs) were picked in the sequence data through QIIME version 1.9.1, and bacteria were classified based on homology of 97% or more with the standard sequences registered in the Greengenes database.

Figure 4:
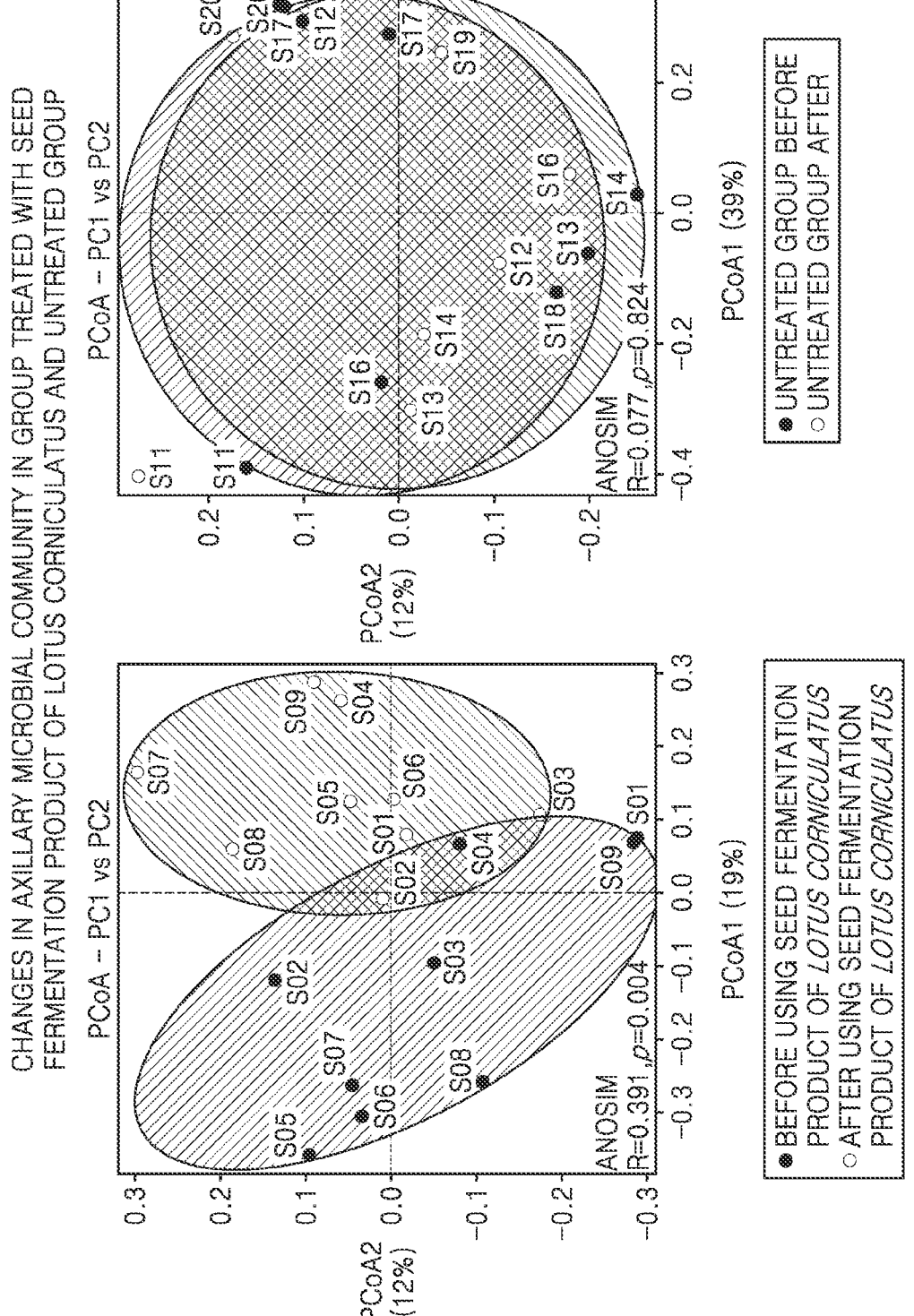
FIG. 4 shows results of a principal coordinate analysis of changes in the axillary microbiome in a group treated with the seed fermentation product of *Lotus corniculatus* and an untreated group.

FIG. 4 shows changes in the microbiomes of 17 subjects who participated in the experiment through a method of a principal coordinate analysis (PCoA). According to FIG. 4, the difference in the microbiomes before and after the use of the fermentation product was clear in the group treated with the fermentation product of *Lotus corniculatus*. Specifically, the coordinate positions changed significantly before and after the use of the seed extract of *Lotus corniculatus* (refer to the red circle and blue circle in FIG. 4), and sizes and positions of the area that combined coordinate positions also changed significantly (refer to the red area and blue area in FIG. 4). As a result of an analysis of similarities (ANOSIM), there was a statistically significant difference in the microbiome before and after the use of the seed fermentation product of *Lotus corniculatus*. On the other hand, the microbiomes of the untreated group did not show a significant difference in coordinate positions and areas before and after participating in the experiment, and did not show a statistically significant difference in the results of ANOSIM.

Figure 5:
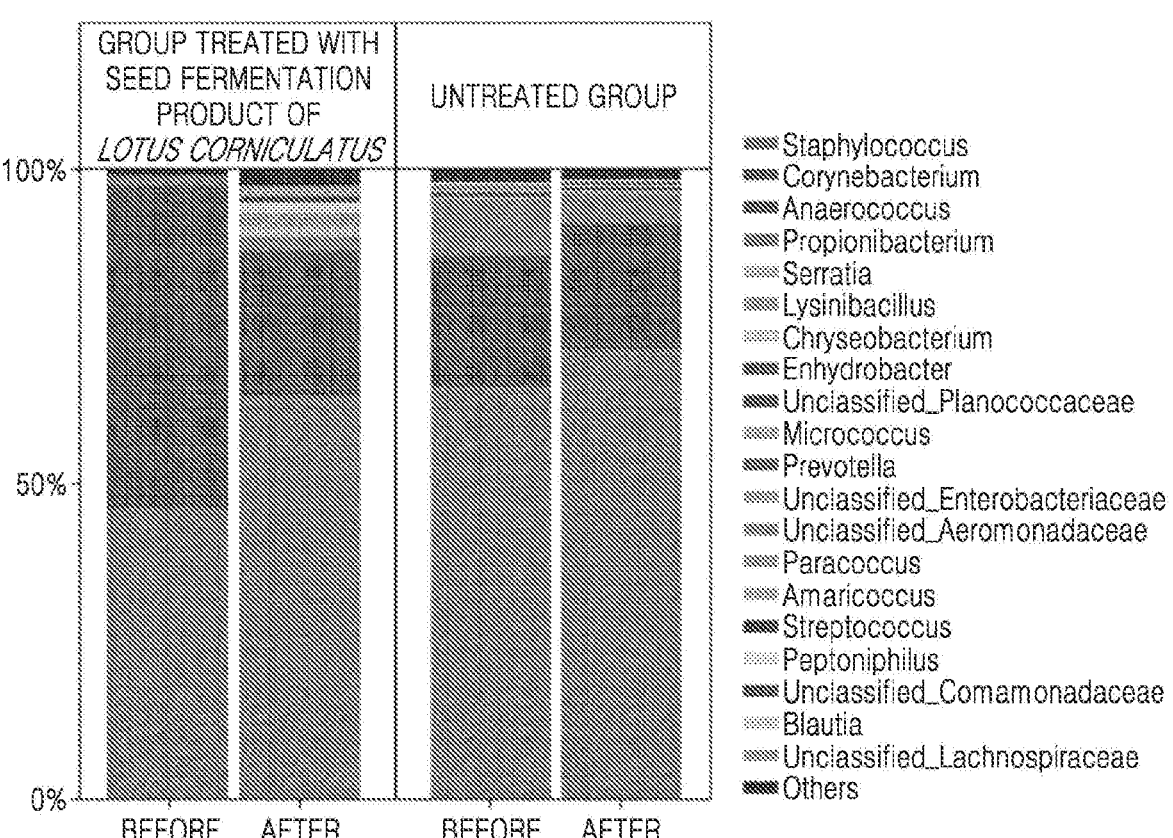
FIG. 5 shows changes in the axillary skin microbiome of subjects who used the seed fermentation product of *Lotus corniculatus* according to an embodiment.

FIG. 5 shows average values of ratio of constituents of each of the microbiomes of nine people in the group treated with the seed fermentation product of *Lotus corniculatus* and eight people in the untreated group. According to FIG. 5, when the seed fermentation product of *Lotus corniculatus* was treated, microorganisms of the genus *Corynebacterium* and *Anaerococcus* that cause odors in the microbiome were relatively reduced. On the other hand, strains belonging to the genus *Staphylococcus* increased. On the other hand, the proportion of microorganisms in the microbiome did not change significantly in the untreated group.

However, even though the two kinds of microorganisms of the genus *Corynebacterium* and the genus *Anaerococcus* were reduced by using the seed fermentation product of *Lotus corniculatus*, it may not be concluded that these results are due to the direct antibacterial or activity inhibitory effect against the strains. This is because a reduction of a specific kind of microorganisms in a microbiome may be caused by an increase in a community of other microorganisms or a change in an activity of a third kind of microorganisms interacting with the reduced microorganisms.

Summarizing the above experimental results, it is judged that the seed fermentation product of *Lotus corniculatus* may reduce proportions of bacteria of the genus *Coryne-*

*bacterium* and the genus *Anaerococcus* that produce odorous substances in the microbiome, and thus have an effect of ameliorating bromhidrosis.

So far, the present disclosure has been described focusing on the examples. Those skilled in the art to which the present disclosure pertains will be able to understand that the present disclosure may be implemented in a modified form without departing from the essential characteristics of the present disclosure. Therefore, the disclosed embodiments should be considered from an illustrative rather than a limiting point of view. The scope of the present disclosure is shown in the claims rather than the above-described description, and all differences within an equivalent range thereto should be construed as being included in the present disclosure.

The invention claimed is:

1. A method of treating bromhidrosis, comprising administering to a subject in need thereof a composition comprising a seed fermentation product of a plant belonging to the genus *Lotus*.

2. The method of claim 1, wherein the seed fermentation product of a plant belonging to the genus *Lotus* inhibits decomposition activity of microorganisms belonging to the genus *Corynebacterium* and microorganisms belonging to the genus *Anaerococcus*.

3. The method of claim 1, wherein the seed fermentation product of a plant belonging to the genus *Lotus* is fermented with lactic acid bacteria.

4. The method of claim 3, wherein the lactic acid bacteria are *Lactobacillus acidophilus*.

5. The method of claim 1, wherein the seed fermentation product of a plant belonging to the genus *Lotus* is fermented for about 3 days to about 7 days at about 35° C. to about 37° C.

6. The method of claim 1, wherein the composition is formulated as an external skin preparation.

* * * * *